US012564691B2

(12) United States Patent
Litke et al.

(10) Patent No.: US 12,564,691 B2
(45) Date of Patent: Mar. 3, 2026

(54) MEDICAL DEVICE INSUFFLATION CONNECTION

(71) Applicant: Intuitive Surgical Operations, Inc., Sunnyvale, CA (US)

(72) Inventors: Ronald G. Litke, Sandy Hook, CT (US); Justin Krom, Southington, CT (US); Joseph P. Orban, III, Norwalk, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 86 days.

(21) Appl. No.: 17/429,886

(22) PCT Filed: Feb. 10, 2020

(86) PCT No.: PCT/US2020/017561
§ 371 (c)(1),
(2) Date: Aug. 10, 2021

(87) PCT Pub. No.: WO2020/167697
PCT Pub. Date: Aug. 20, 2020

(65) Prior Publication Data
US 2022/0203048 A1      Jun. 30, 2022

Related U.S. Application Data

(60) Provisional application No. 62/803,985, filed on Feb. 11, 2019.

(51) Int. Cl.
*A61M 13/00*      (2006.01)
*A61M 39/10*      (2006.01)
(52) U.S. Cl.
CPC .......... *A61M 13/003* (2013.01); *A61M 39/10* (2013.01); *A61M 2205/3334* (2013.01); *A61M 2205/3344* (2013.01)

(58) Field of Classification Search
CPC . A61B 17/3474; A61B 17/3439; A61B 17/34; A61B 17/3423; A61M 13/003;
(Continued)

(56) References Cited

U.S. PATENT DOCUMENTS 2,244,334 A      6/1941  Hopkins
2,435,480 A      2/1948  John et al.
(Continued)

FOREIGN PATENT DOCUMENTS

WO      WO-2017034965 A1      3/2017
WO      WO-2018097738 A1      5/2018

OTHER PUBLICATIONS

International Preliminary Report on Patentability for Application No. PCT/US2020/017560, mailed on Aug. 26, 2021, 11 pages.
(Continued)

*Primary Examiner* — Kami A Bosworth
*Assistant Examiner* — Avery Smale
(74) *Attorney, Agent, or Firm* — Schwegman, Lundberg & Woessner, P.A.

(57)      ABSTRACT

A medical device includes a device body and an insufflation fitting coupled to and extending from the device body. The insufflation fitting includes an annular high-flow fitting portion and an annular low-flow fitting portion extending away from the device body from the annular high-flow fitting portion. The annular high-flow fitting portion includes a first inner surface and a radially outward sealing surface generally reverse from the first inner surface. The annular low-flow fitting portion includes an inner sealing surface and a first radially outward surface generally reverse from the inner sealing surface. The first inner surface of the annular high-flow fitting portion and the inner sealing surface of the annular low-flow fitting portion define an insufflation gas flow passageway through the insufflation fitting.

17 Claims, 13 Drawing Sheets

(58) Field of Classification Search
CPC .. A61M 2205/3334; A61M 2205/3344; A61M 39/1011; A61M 2039/1077; A61M 39/12; A61M 13/00; A61M 13/006; A61M 39/02; A61M 2039/0205; A61M 39/0247; A61M 2039/0264; A61M 2039/0276; A61M 2039/0279; A61M 2039/0288; A61M 2039/1033; A61M 2039/1038; A61M 39/105; A61M 2039/1083; A61M 2039/1088; A61M 39/10
See application file for complete search history.

(56) References Cited

U.S. PATENT DOCUMENTS

| | | | |
|---|---|---|---|
| 2,894,630 A | | 7/1959 | Humbert, Jr. et al. |
| 4,046,145 A | | 9/1977 | Choksi et al. |
| 4,263,922 A | | 4/1981 | White |
| 4,349,024 A | | 9/1982 | Ralston, Jr. et al. |
| 5,047,021 A | * | 9/1991 | Utterberg ................ F16L 33/24 |
| | | | 604/905 |
| 5,267,983 A | | 12/1993 | Oilschlager et al. |
| 5,569,222 A | | 10/1996 | Haselhorst et al. |
| 6,508,807 B1 | | 1/2003 | Peters |
| 9,387,295 B1 | | 7/2016 | Mastri et al. |
| 10,960,197 B2 | | 3/2021 | Zergiebel et al. |
| 2004/0230161 A1 | | 11/2004 | Zeiner |
| 2006/0025749 A1 | | 2/2006 | Moenning |
| 2006/0271015 A1 | | 11/2006 | Mantell |
| 2007/0129705 A1 | * | 6/2007 | Trombley, III ....... A61M 39/10 |
| | | | 604/523 |
| 2013/0046287 A1 | * | 2/2013 | Davis ................. A61M 39/1011 |
| | | | 604/535 |
| 2014/0171855 A1 | | 6/2014 | Mastri et al. |
| 2016/0296740 A1 | | 10/2016 | Adams et al. |
| 2017/0014616 A1 | | 1/2017 | Davis et al. |
| 2018/0008812 A1 | * | 1/2018 | Roxas ................... A61M 1/367 |
| 2018/0056056 A1 | | 3/2018 | Law et al. |
| 2018/0256830 A1 | | 9/2018 | Silver et al. |
| 2021/0187265 A1 | | 6/2021 | Schuler |

OTHER PUBLICATIONS

International Preliminary Report on Patentability for Application No. PCT/US2020/017561, mailed on Aug. 26, 2021, 13 pages.
International Search Report and Written Opinion for Application No. PCT/US2020/017560, mailed May 25, 2020, 15 pages.
International Search Report and Written Opinion for Application No. PCT/US2020/017561, mailed May 28, 2020, 17 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP24217458. 9, mailed on Feb. 19, 2025, 8 pages.

* cited by examiner

MEDICAL DEVICE INSUFFLATION CONNECTION

CLAIM OF PRIORITY

This application is a U.S. National Stage Filing under 35 U.S.C. 371 from International Application No. PCT/US2020/017561, filed on Feb. 10, 2020, and published as WO 2020/167697 A1 on Aug. 20, 2020, which claims the benefit of priority to U.S. Provisional Patent Application No. 62/803,985, filed on Feb. 11, 2019, each of which is incorporated by reference herein in its entirety.

TECHNICAL FIELD

This document relates generally to medical devices, and more particularly, to devices and methods for coupling devices to a source of fluid, such as coupling an instrument seal to an insufflation gas source.

BACKGROUND

A surgical procedure, such as a minimally-invasive laparoscopic surgical procedure, may involve insufflation of a portion of the body with a gas. For example, in a laparoscopic procedure, an insufflation gas may be delivered to the peritoneal cavity of a patient to distend the abdomen, which may improve visual and physical access to internal organs in the abdomen. For example, distension of the patient's abdomen may provide sufficient operating space to enable adequate visualization of the structures and manipulation of instruments inside a patient.

It is important to maintain insufflation gas flow and pressure during a surgical procedure. For example, the interface between surgical equipment and an access orifice in the patient's body should be sealed to avoid or reduce leakage of insufflation gas, so that insufflation can be maintained. When a system has a leak, additional insufflation gas may be needed to maintain insufflation through the procedure (e.g., to make up for leaked insufflation gas).

In a minimally invasive surgical procedure, such as a laparoscopic procedure, one or more cannulas may be used to deliver surgical tools into a body cavity. A cannula seal is typically used to contain insufflation gas pressure within a body cavity, whether an instrument is inserted or not, to avoid or reduce leakage of insufflation gas through the cannula during the procedure. A source of insufflation gas may be coupled to a medical device, such as a cannula seal, to deliver insufflation pressure during a procedure.

SUMMARY

An example medical device includes a device body and an insufflation fitting coupled to and extending from the device body. The insufflation fitting includes an annular high-flow fitting portion and an annular low-flow fitting portion extending away from the device body from the annular high-flow fitting portion. The annular high-flow fitting portion includes a first inner surface and a radially outward sealing surface generally reverse from the first inner surface. The annular low-flow fitting portion includes an inner sealing surface and a first radially outward surface generally reverse from the inner sealing surface. The first inner surface of the annular high-flow fitting portion and the inner sealing surface of the annular low-flow fitting portion define an insufflation gas flow passageway through the insufflation fitting.

A medical device fitting includes an annular high-flow fitting portion and an annular low-flow fitting portion extending away from the high-flow fitting portion. The annular high-flow fitting portion includes a first inner surface and a radially outward sealing surface generally reverse from the first inner surface. The low-flow fitting portion includes an inner sealing surface and a first radially outward surface generally reverse from the inner sealing surface. The first inner surface of the annular high-flow fitting portion and the inner sealing surface of the annular low-flow fitting portion define a fluid flow passageway. A high-flow connector surrounds the low-flow fitting portion and includes an inner female sealing surface in sealing engagement with the radially outward sealing surface of the annular high-flow fitting portion.

Another medical device fitting includes an annular high-flow fitting portion and an annular low-flow fitting portion extending away from the high-flow fitting portion. The annular high-flow fitting portion includes a first inner surface and a radially outward sealing surface generally reverse from the first inner surface. The low-flow fitting portion includes an inner sealing surface and a first radially outward surface generally reverse from the inner sealing surface. The first inner surface of the annular high-flow fitting portion and the inner sealing surface of the annular low-flow fitting portion define a fluid flow passageway.

A medical device includes a fluid connector including means for receiving a relatively low flow fluid connector and means for receiving a relatively high flow fluid connector. The means for receiving a relatively high fluid flow connector includes a male sealing surface coaxially aligned with the means for receiving a relatively low flow fluid connector.

Each of these non-limiting examples can stand on its own or can be combined in various permutations or combinations with one or more of the other examples.

This Summary is intended to provide an overview of subject matter of the present patent application. It is not intended to provide an exclusive or exhaustive explanation of the invention. The detailed description is included to provide further information about various aspects of the inventive subject matter of the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
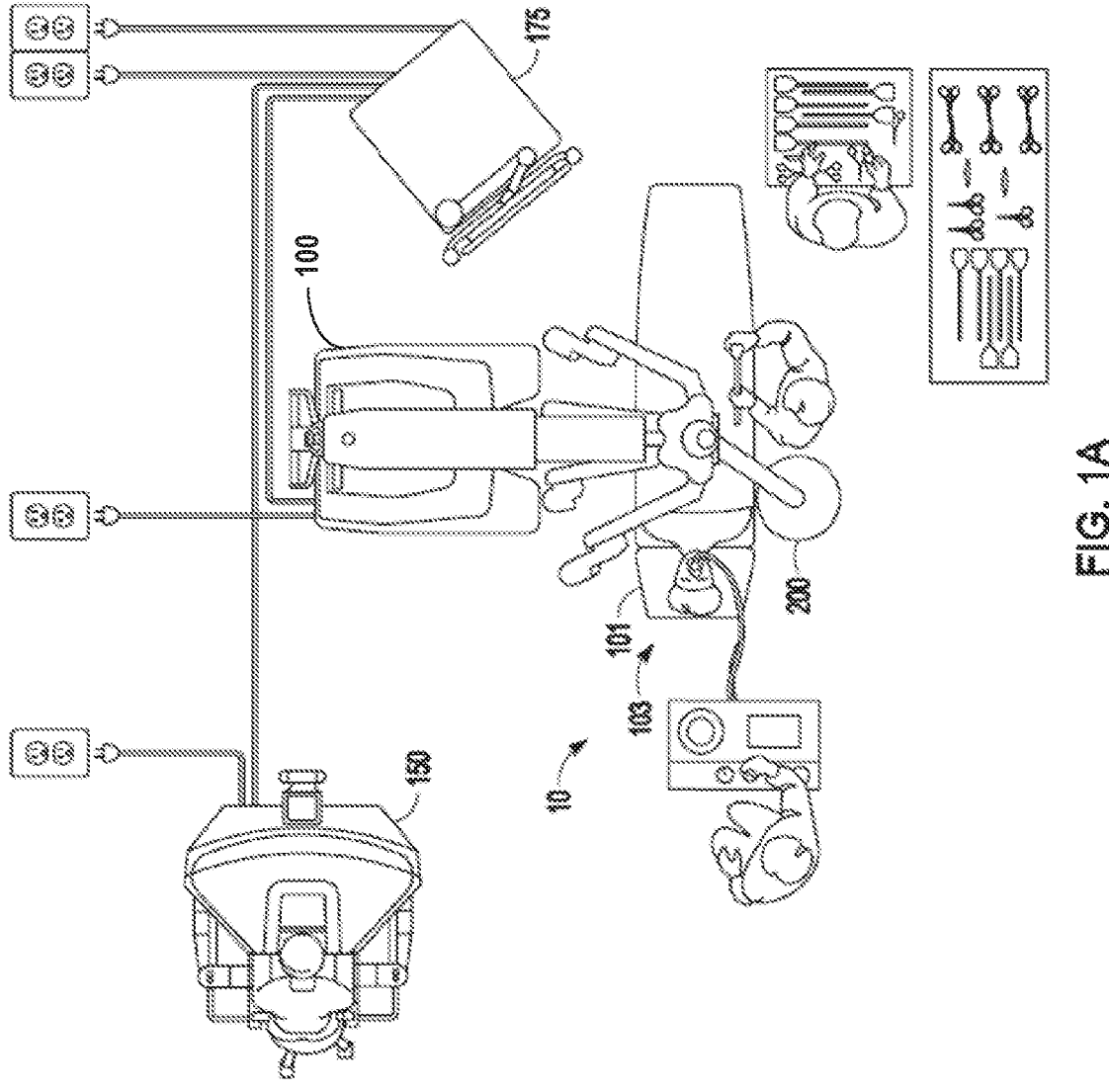
FIG. 1A is a plan view illustration of an example medical system in a surgical environment.

As noted above, it is important to maintain insufflation gas flow and pressure during a surgical procedure. In some cases, however, it may also be important to not exceed a threshold flow parameter, such as flow rates, flow volumes, insufflation pressures, etc. As an example, it may be important to not exceed an insufflation pressure of 80 mm HG 8.0 (1.55 PSI). At this maximum pressure below, however, it is still possible to vary the flow rate and/or volume, and it may be desirable to increase the flow rate and/or volume.

For example, a higher fluid flow rate/volume may be desirable or required in the event there is a leak in the system, or if there is another source of gas escape through the system. Higher flow may allow the system to keep up with need for flow to maintain sufficient insufflation. An example of a particular application may be in trans-anal procedures in the colon. Insufflation applications that involve smaller body cavities may be improved with higher flow, because it is generally easier to insufflate smaller body cavities with more flow. Additionally, if there's less volume in the cavity, a leak (or other gas escape) impacts the volume more quickly, and higher flow affords more time to respond to such situations and to thereby return to a proper or prescribed insufflation state as soon as possible.

One standard fitting that can be used in insufflation applications is the so-called Luer-type fitting ("Luer taper"). The Luer taper is a standardized system for certain fluid fittings used for making connections between a male-taper fitting and its mating female counterpart on medical and laboratory instruments. With standard Luer-type fittings (and other standard fittings), there's a limit to fluid flow through the fitting, which is dictated at least in part on the minimum diameter of the flow channel formed when the fittings are coupled together. In the Luer-type fitting this minimum diameter is typically the inner diameter of the tapered male Luer-type fitting.

Since Luer-type fittings are a standard in the medical device industry, current medical devices are typically designed to fit such standard fittings, including the so-called Luer-type fittings. This common design allows devices from different manufacturers (e.g., sources of insufflation gas, vacuum, or irrigation liquid, etc.; cannula seal connections, suction/irrigation instruments, etc.) to be coupled together. But since such standard fittings have fluid flow limits, a new fitting may advantageously be configured to adapt/couple to both a higher flow fitting and to a standardized low-flow Luer-type fitting for retrofit capability.

In one example in accordance with this disclosure, a medical device includes a device body and an insufflation fitting. The insufflation fitting is coupled to and extends from the device body. the insufflation fitting includes an annular low-flow fitting and an annular high-flow fitting. The annular low-flow fitting has a radially outward surface generally opposed to a first inner sealing surface. The inner sealing surface defines a flow passageway for insufflation gas. The annular high-flow fitting has a second inner sealing surface extending around and radially offset from the radially outward surface of the low-flow fitting.

In another example in accordance with this disclosure, a medical device includes a device body and an insufflation fitting. The insufflation fitting is coupled to and extends from the device body. The insufflation fitting includes an annular high-flow fitting portion and an annular low-flow fitting portion. The annular high-flow fitting portion has a radially outward sealing surface generally opposed to a first inner surface. The annular low-flow fitting portion extends away from the device body from the high-flow fitting portion. The low-flow fitting portion includes a first radially outward surface generally opposed to an inner sealing surface, the first inner surface and the inner sealing surface defining a flow passageway for insufflation gas.

FIG. 1A is a plan view depicting an example medical procedure environment that includes a multi-arm manipulating system 100 adjacent to a surgical table 101 that supports a patient 103. A second manipulating system 200 may also be situated at the surgical table 101. The manipulating systems 100, 200 may be free-standing on a movable base, or they may be mounted to a table, floor, wall, or ceiling, or they may be supported on another piece of equipment in the clinical environment.

The manipulating system 100 or system 200 may be part of a larger system 10, which may include other sub-systems, including, for example, fluoroscopy or other imaging equipment. One or both of the manipulating systems 100, 200 may be operatively coupled to a user control system 150 or an auxiliary system 175, or both. The user control system 150 may include one or more user input devices (e.g., controls) that may be configured to receive inputs from a user (e.g., clinician). The user control system 150 may also include or one or more user feedback devices (e.g., viewing system, or tactile or auditory feedback system) that may be configured to provide information to the user regarding the movement or position of an end effector, or an image of a surgical area. The auxiliary system 175 may, for example, include computer processing equipment (e.g., a processor circuit or graphics hardware), or communication equipment (e.g., wired or wireless communication circuits), or endoscopic camera control and image processing equipment.

Figure 1B:
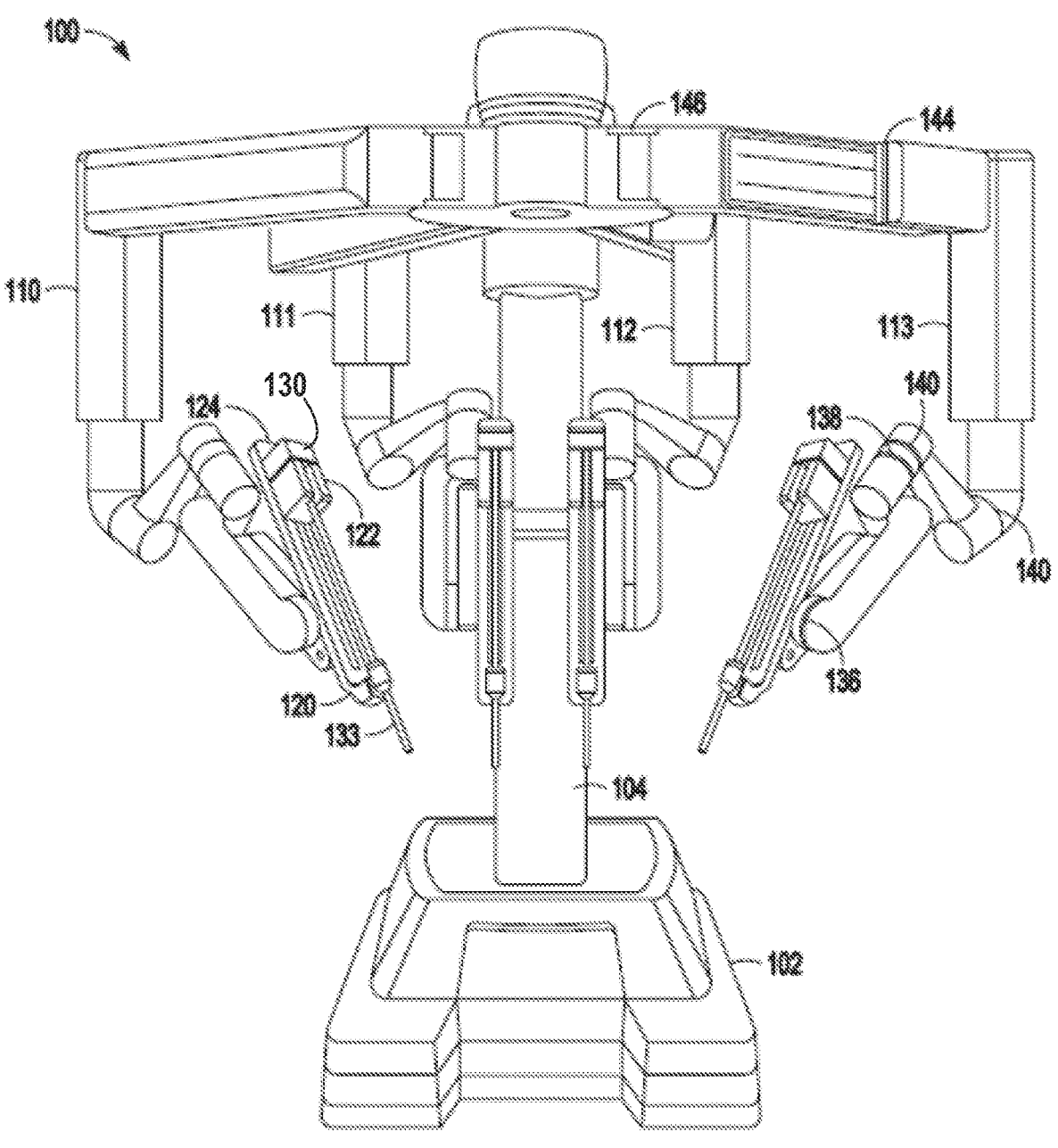
FIG. 1B is an illustration of an example manipulating system.

FIG. 1B depicts example manipulating system 100. The example manipulating system 100 includes a base 102, a support tower 104, and one or more manipulator arms 110, 111, 112, 113, which may be mounted on the support tower 104. An instrument 130 (shown in more detail in FIG. 1E) is mounted to an instrument mount 120 on one of the manipulator arms 110-113. The instrument mount 120 includes, as an example, an instrument carriage 122, which is mounted to a spar 124, which may be a telescoping or non-telescoping spar. A cannula 133 may be mounted to a cannula mount 126, and the instrument 130 may be inserted through a cannula seal in the cannula 133, and into the patient 103 (FIG. 1A) for use in a therapeutic or diagnostic surgical procedure. Through movement of the manipulator arms 110-113, the translation and orientation of the instrument 130 may be controlled in multiple mechanical degrees of freedom, e.g. lateral, horizontal, vertical, angular movements in one, two, or three planes. The system 100 may include one or more light features 136, 138, 140, 142, 144, 146 at one or more of a variety of locations on the manipulator arms 110-113 (i.e., at joints between arm links, as shown).

Cannula 133 may be inserted into the patient 103, and a surgical instrument seal assembly (not shown) is inserted into the cannula. The instrument seal prevents insufflation gas from escaping through the open cannula when no instrument is inserted in the cannula, and it also prevents insufflation gas from escaping between the instrument shaft and the cannula inner wall when an instrument is inserted in the cannula.

Figure 1C:
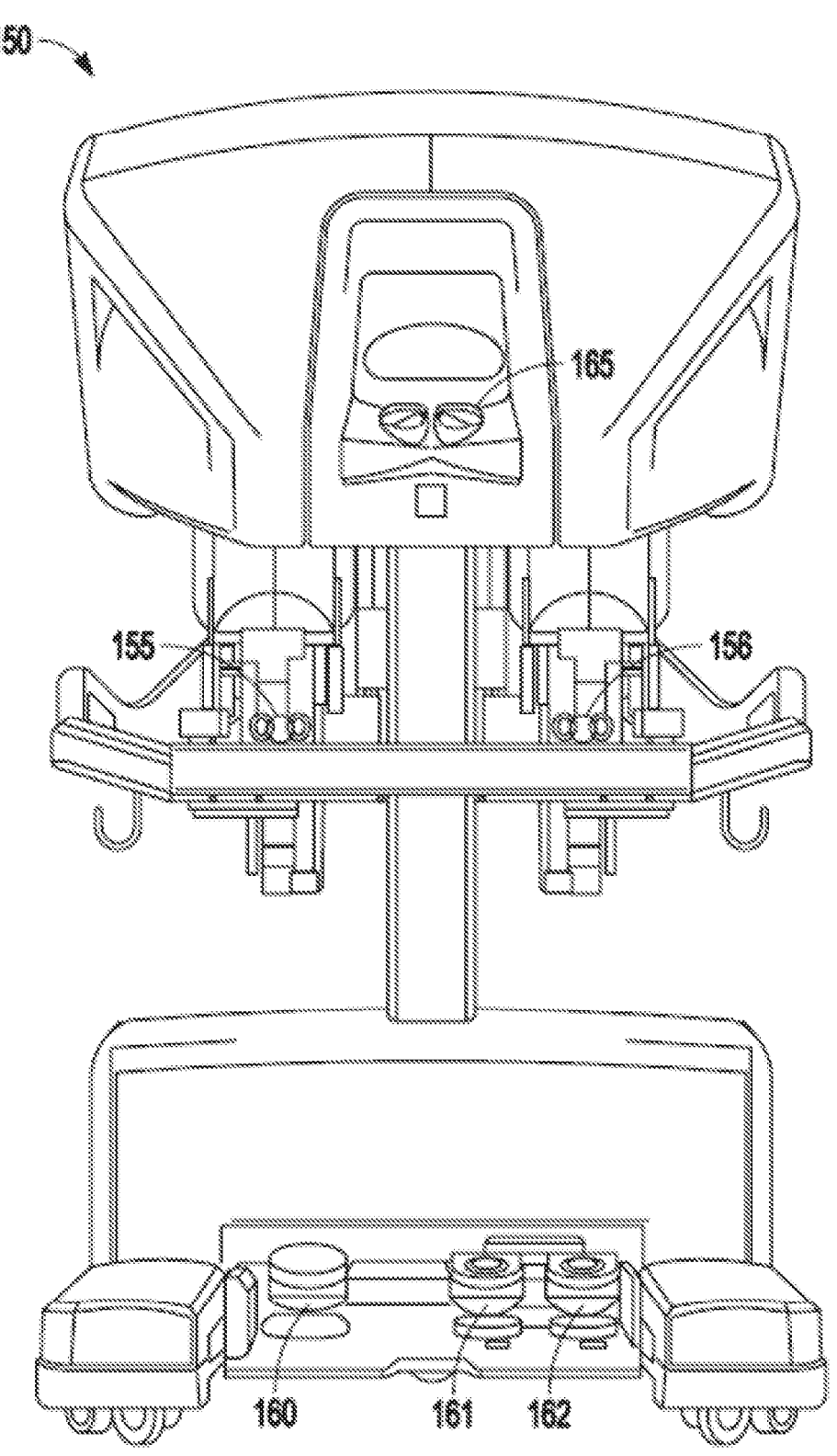
FIG. 1C is an illustration of an example user control system.

FIG. 1C depicts example user control system 150. The user control system 150 includes hand controls 155, 156 and foot pedal controls 160, 161, 162. The hand controls 155, 156 and foot pedal controls 160, 161, 162 are used to control equipment at one or more of the manipulating systems 100, 200. For example, an operator may manipulate portions of a distal end of an instrument 130 by using the instrument controls. The controls may include haptic feedback features so that a surgeon may interpret physical information at the instrument 130, such as resistance or vibration, through the controls. The user control system 150 may also include a viewing system 165 that displays video or other images of a surgical site.

Figure 1D:
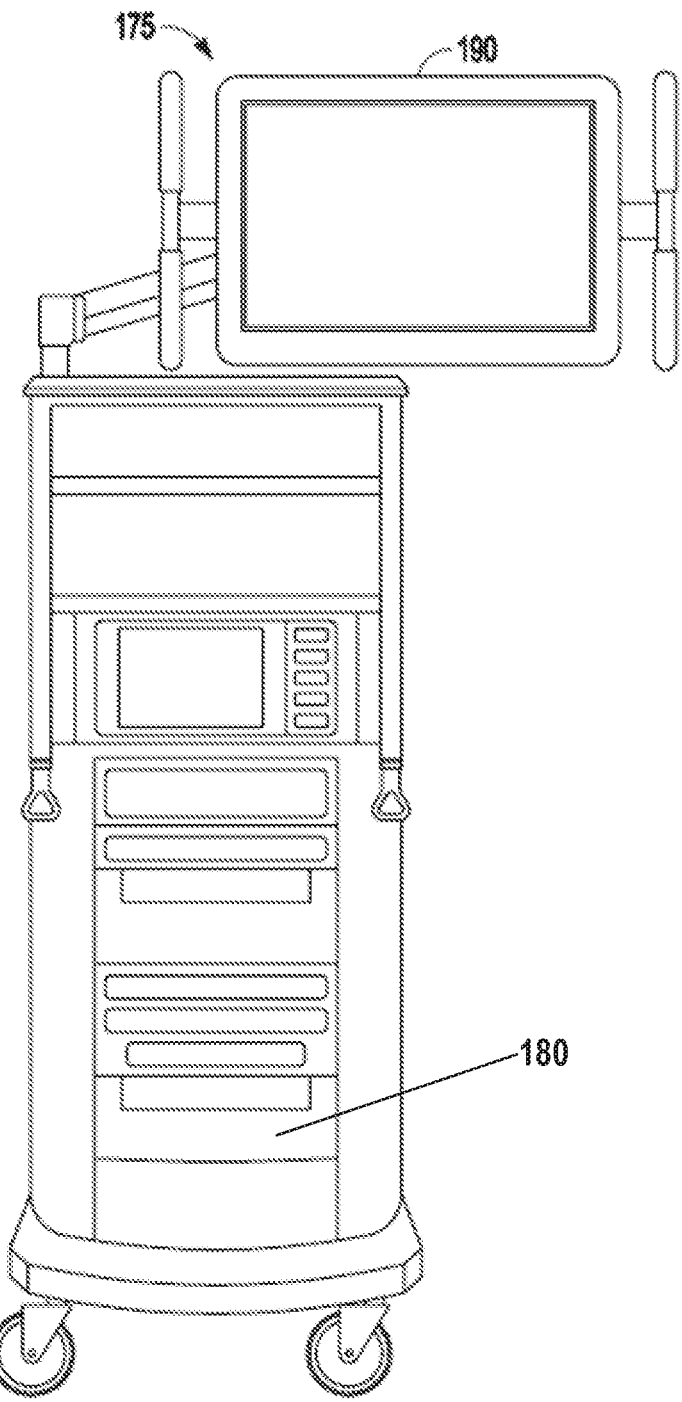
FIG. 1D is an illustration of an example auxiliary system.

FIG. 1D depicts an example auxiliary system 175. The example auxiliary system 175 optionally includes telesurgical system functions that are not incorporated into other system units, such as computer processing system 180 for processing teleoperation controls, facilitating communication between the user control system and the manipulating system, or a remote site, endoscopic camera control and illumination, electrosurgical generation and control, etc. The auxiliary system 175 may also include a display 190, which shows images that the user (e.g., a clinician) is seeing on the user control system 150, a video feed from a camera in the patient 103, or other information. In an example configuration, signals input at a user control system 150 may be transmitted to the processing system 180 on the auxiliary system 175, which interprets the inputs and generate commands that are transmitted to the manipulating system 100 to cause manipulation of an instrument 130 or portions of a manipulator arm 110. The processing system 180 is shown on a cart for exemplary purposes, but it may also be arranged in various configurations, e.g., it may be integrated as part of the user control system 150, the manipulating system 100, 200, or both, or divided between the user control system 150 and manipulating system 100, 200. The equipment may also be provided as software, hardware, or both, on an installed or remote system.

Figure 1E:
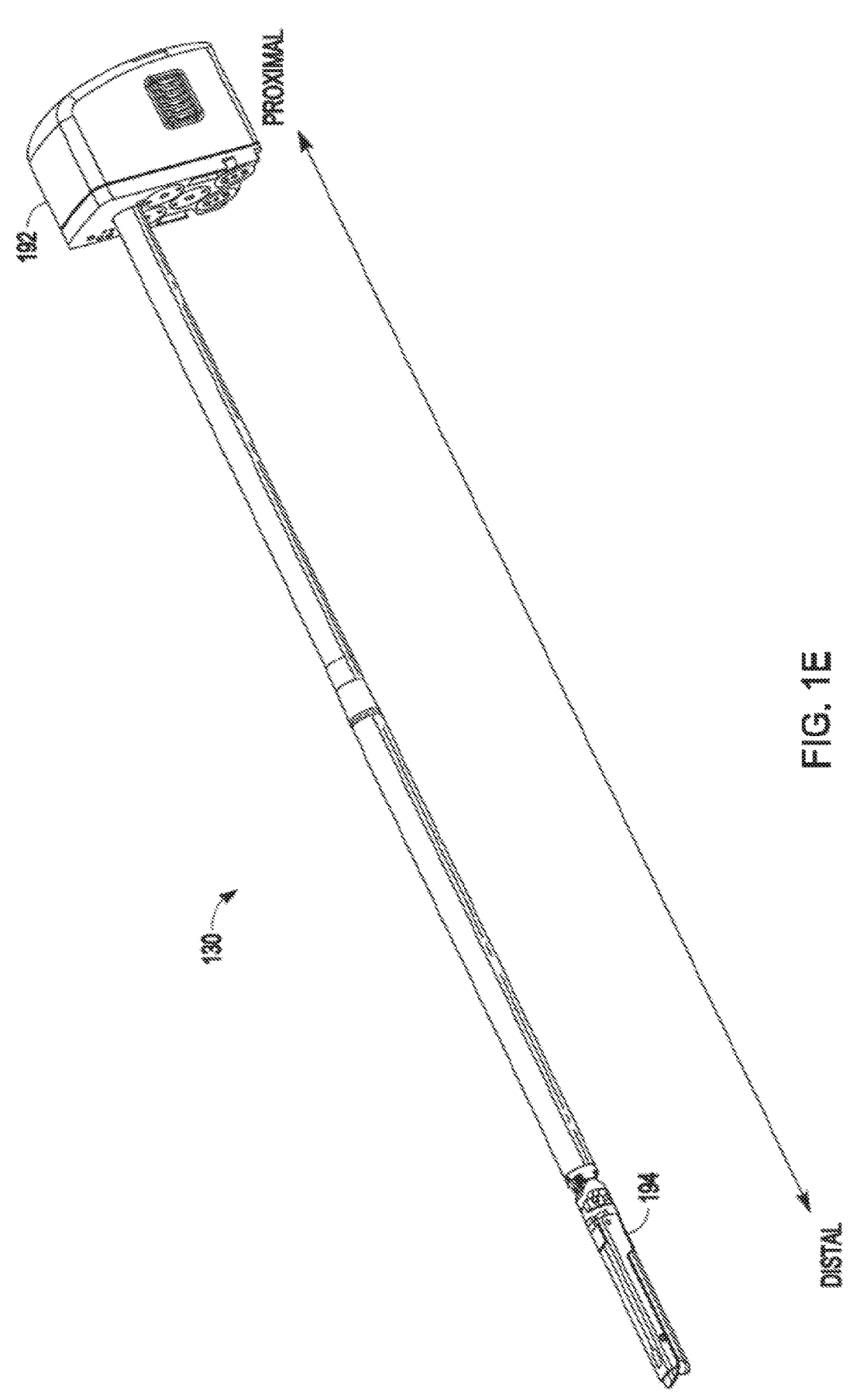
FIG. 1E is an illustration of an example instrument.

FIG. 1E depicts example instrument 130. The instrument 130 includes a proximal portion 192, which is configured to couple to an instrument mount on a manipulator arm. The instrument 130 also includes a distal portion 194 and an instrument shaft 196 between the proximal portion 192 and the distal portion 194. The distal portion 194 shown is a stapler, and in other instruments it may be a cautery tool, cutter, camera, or other medically relevant end effector. The instrument 130 may be teleoperatively controlled via command signals received from a control computer, such as a user control system 150 or auxiliary system 175 to conduct a surgical procedure. Inputs may be received from a user (e.g., clinician), and the instrument 130 may be controlled based on the user inputs.

In an example, instrument 130 is inserted into the patient 130 via cannula 133, which also contains a surgical instrument seal assembly as described above. In such a procedure, it may be important to provide and maintain insufflation of a body cavity of the patient 130.

Figure 2A:
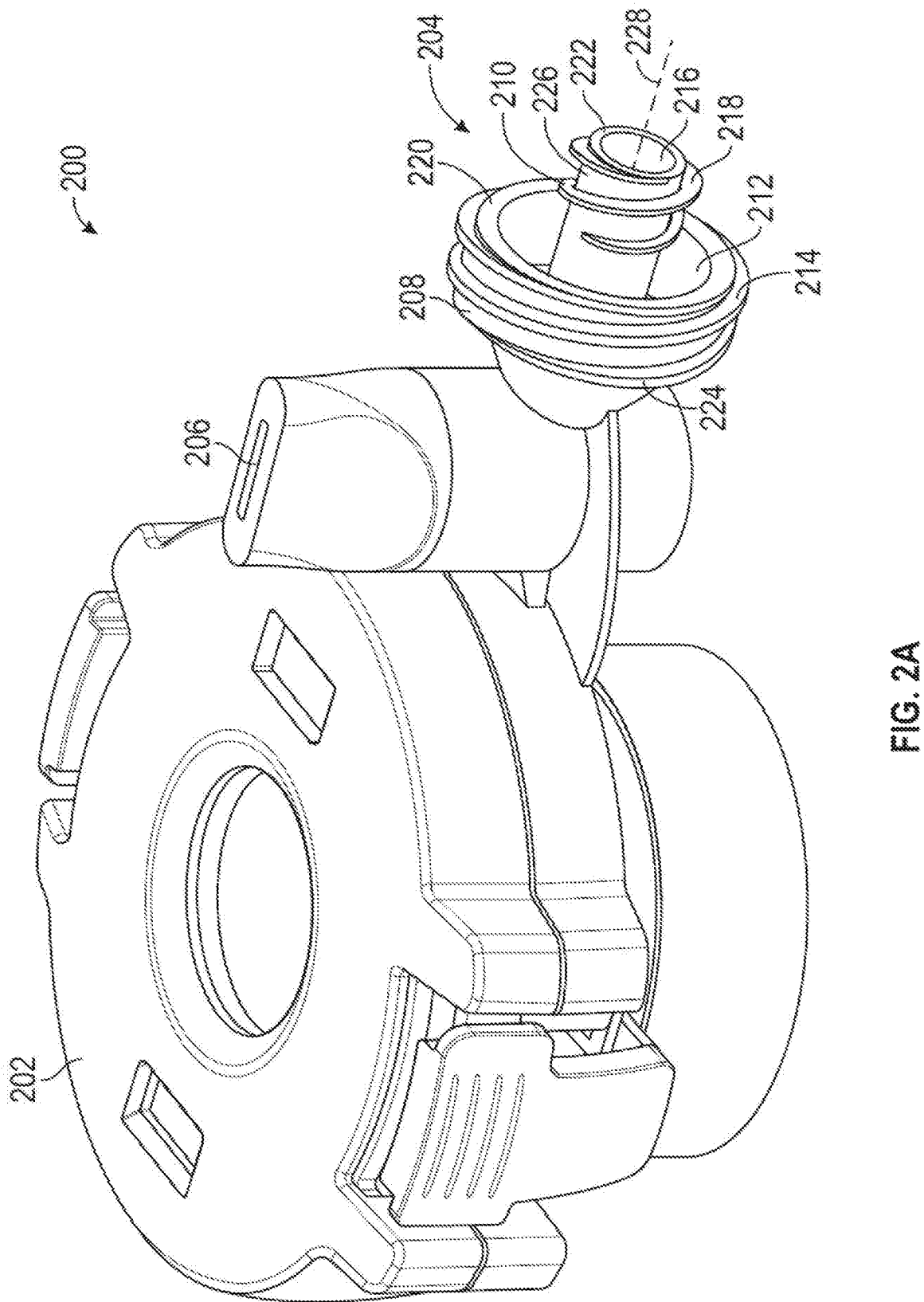
FIG. 2A is a perspective view depicting an example surgical instrument seal assembly.
Figure 2B:
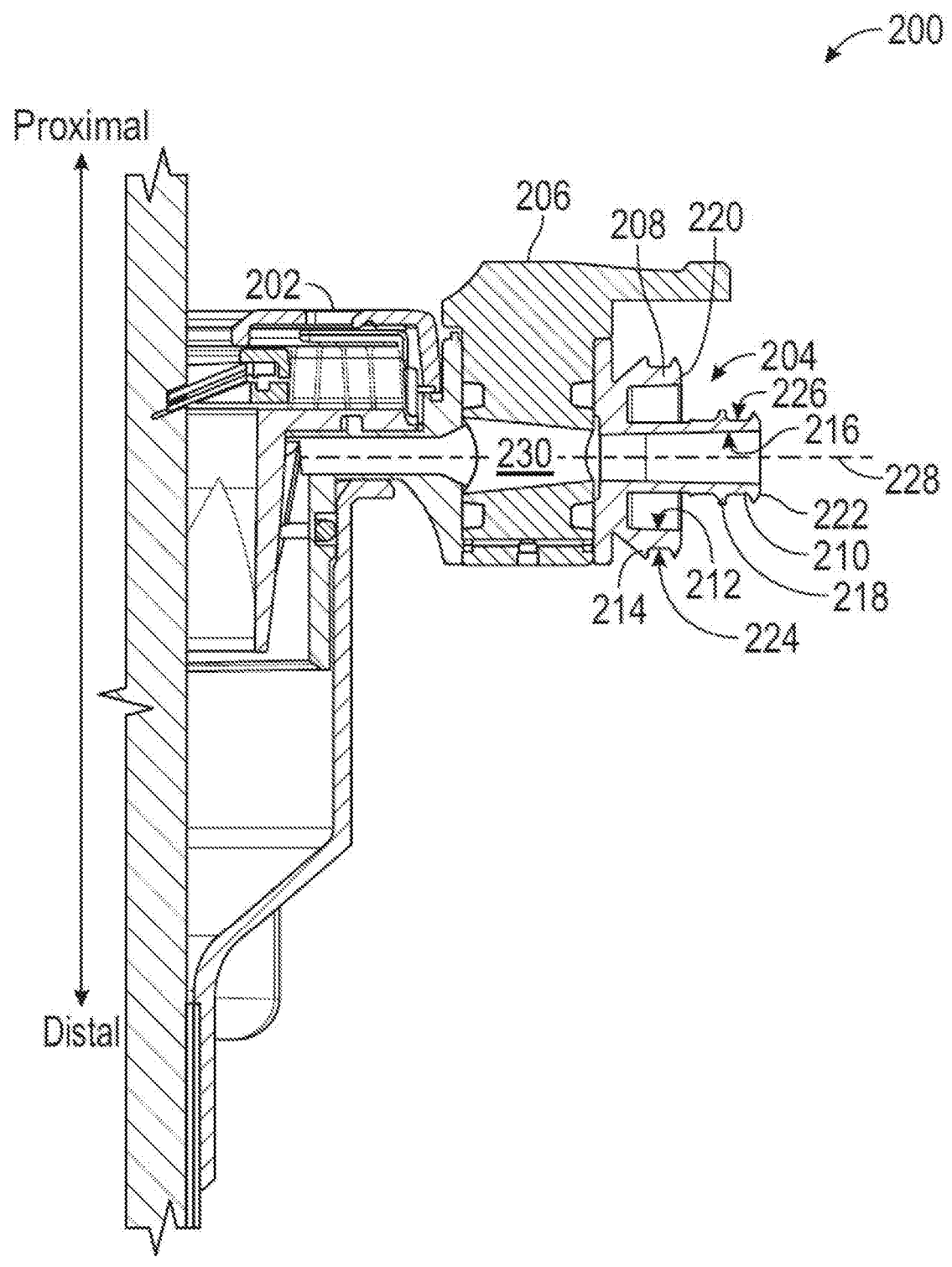
FIG. 2B is a cross-section elevation view depicting the example surgical instrument seal assembly of FIG. 2A.

FIG. 2A is a perspective view depicting example surgical instrument seal assembly 200. FIG. 2B is a cross-section elevation view depicting example surgical instrument seal assembly 200. Referring to FIGS. 2A and 2B, instrument seal assembly 200 includes device body 202, insufflation fitting 204, and valve 206. Valve 206 is fluidically connected to the fluid passageway of insufflation fitting 204 and configured to control the flow of insufflation gas into device body 202. Valve 206 can be a variety of different valves, including a stopcock valve as depicted in the example of FIGS. 2A and 2B.

Insufflation fitting 204 extends from device body 202, and a flow passage is defined through fitting 204 and into device body 202. Insufflation fitting 204 includes high-flow fitting 208 and low-flow fitting 210. In this disclosure, high-flow is a rate and/or volume of flow that is higher relative to low-flow. In the case of insufflation fitting 204 and other such fittings in accordance with this disclosure, for a constant fluid pressure high-flow fitting 208 provides or enables a higher rate and/or volume of flow of fluid than low-flow fitting 210. In some examples, high-flow fitting 208 and low-flow fitting 210 are fabricated integral with one another to form insufflation fitting 204 in accordance with this disclosure. In another example, however, low-flow fitting 210 may be fabricated as a separate component and then be coupled to high-flow fitting 208. For example, low-flow fitting 210 may be fabricated as a separate component and then be coupled to high-flow fitting 208 using, for example, an adhesive or by welding low-flow fitting 210 to high-flow fitting 208.

In the example of insufflation fitting 204, high-flow fitting 208 includes first internal/inner (sometimes referred to as "female") sealing surface 212. and first coupling portion 214. Low-flow fitting 210 includes second internal/inner sealing surface 216 and second coupling portion 218. First sealing surface 212 of high-flow fitting 208 is a female tapered surface, the diameter of which decreases from free end 220 of high-flow fitting 208 toward valve 206 and device body 202. Additionally, first sealing surface 212 is an annular sealing surface. Similarly, second sealing surface 216 of low-flow fitting 210 is a female tapered surface, the diameter of which decreases from free end 222 of low-flow fitting 210 toward high-flow fitting 208, valve 206, and device body 202. Second sealing surface 216 is also an annular sealing surface.

First coupling portion 214 is on first external surface 224 of high-flow fitting 208, which external surface is generally reverse of first internal sealing surface 212. Second coupling portion 218 is on second external surface 226 of low-flow fitting 210, which external surface is generally reverse to second internal sealing surface 216. First coupling portion 214 of high-flow fitting 208 and second coupling portion 218 of low-flow fitting 210 include threads. In one example, first coupling portion 214 and second coupling portion 218 include Luer-type threads. In another example, first coupling portion 214 and second coupling portion 218 include another type of thread, lugs, or another locking/coupling mechanism.

Low-flow fitting 210 is concentric with and nested partially within high-flow fitting 208. High-flow fitting 208 and low-flow fitting 210 share a common centerline axis 228, which also defines a flow path centerline through the flow passage 230 of insufflation fitting 204. High-flow fitting 208 is an annulus including first external surface 224 and first internal sealing surface 212, which extend from body 202 of instrument seal assembly 200 to free end 220 of high-flow fitting 208. Low-flow fitting 210 is an annulus including second external surface 226 and second internal sealing surface 216, which extend from body 202 within the annular internal sealing surface 212 of high-flow fitting 208 to free end 222 of low-flow fitting 210.

Although insufflation fitting 204 is depicted in association with an instrument seal assembly/access port device, in other examples fittings in accordance with this disclosure may be used in association with various other medical devices that supply or receive gaseous or liquid fluids. Such medical devices may be used for various medical functions such as body or irrigation fluid suction, smoke evacuation, irrigation fluid supply, supplemental oxygen supply, endoscope lens cleaning and defogging, etc.

Therefore, in accordance with an inventive aspect a standard medical device fitting, such as female Luer-type fitting, is surrounded by a concentric second female fitting. The female Luer-type fitting receives a corresponding male Luer-type fitting to establish a fluid flow path through the coupled female and male Luer-type fittings, but as explained below this flow path is restricted by the Luer-type fitting design. And so the surrounding second female fitting can receive a corresponding second male fitting to establish a fluid flow path through the standard female fitting that is not restricted by the standard female/male fitting design.

Figure 2C:
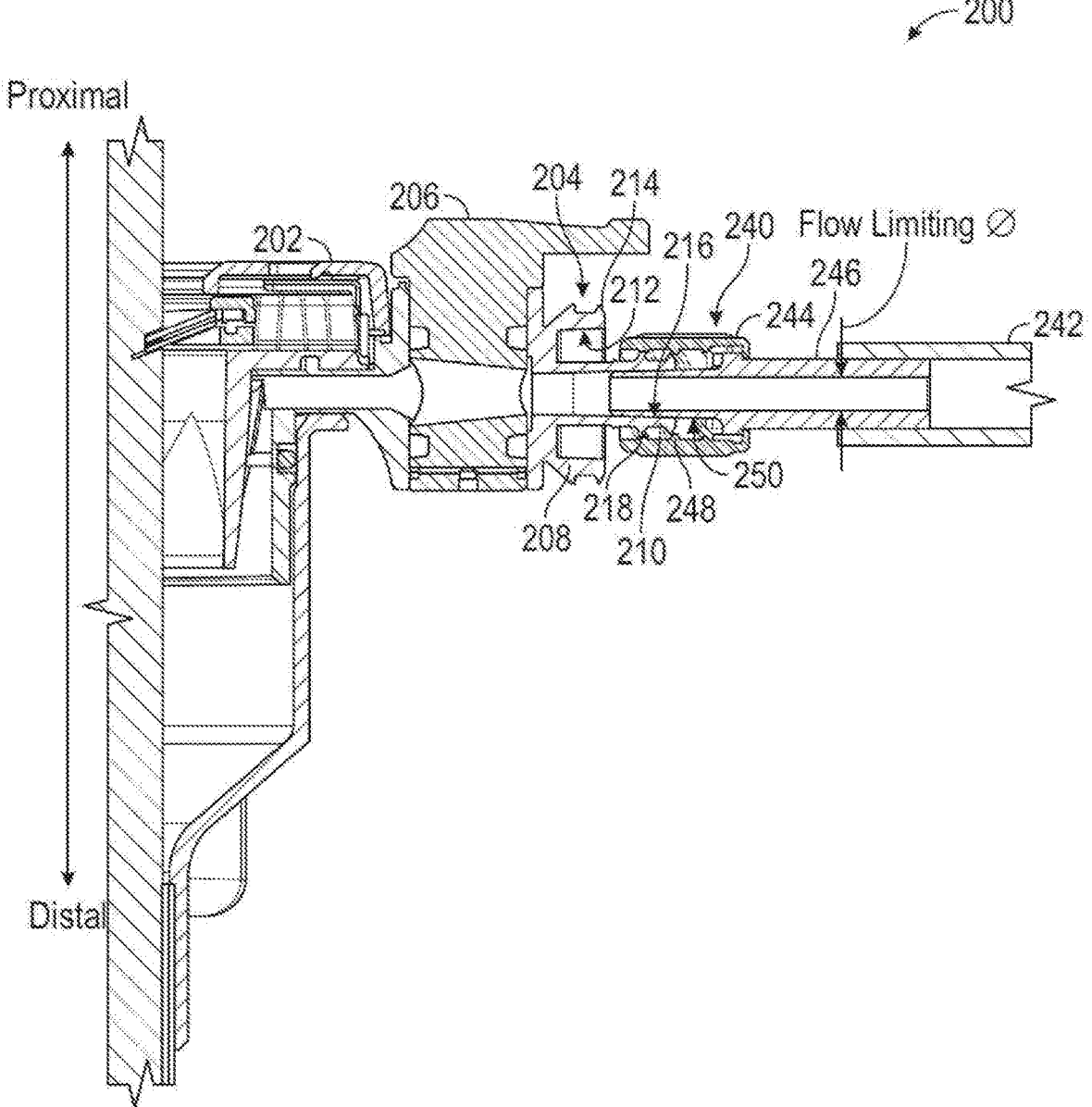
FIG. 2C is a cross-section elevation view depicting the example surgical instrument seal assembly of FIGS. 2A and 2B coupled with a low-flow connector.

FIG. 2C is a cross-section elevation view depicting example surgical instrument seal assembly 200. In FIG. 2C, seal assembly 200 is coupled with a low-flow Luer-type connector 240 connected to low-flow insufflation line 242. The example of FIG. 2C depicts the manner in which insufflation fitting 204 in accordance with this disclosure can be fit to a Luer-type connector 240 for relatively low-flow insufflation (low relative to, e.g., the example of FIG. 2D described below). In particular, the example of FIG. 2C depicts the manner in which low-flow fitting 210 of insufflation fitting 204 can be fit to a Luer-type connector 240 for relatively low-flow insufflation.

Low-flow Luer-type connector 240 includes locking collar 244 coupled to male Luer-type fitting 246, which is coupled to low-flow insufflation gas source line 242. Locking collar 244 includes coupling portion 248, which can include, for example, threads, lugs, or another locking mechanism. Male Luer-type fitting 246 includes external male sealing surface 250. External sealing surface 250 of male Luer-type fitting 246 is a male tapered surface, the diameter of which decreases as external sealing surface 250 extends toward the free end male Luer-type fitting 246. In FIG. 2C, the diameter of external sealing surface 250 decreases as it extends into low-flow fitting 210.

Locking collar 244 is configured to be coupled to low-flow fitting 210 via second coupling portion 218. For example and as depicted in FIG. 2C, coupling portion 248 of locking collar 244 is threadedably engaged to second coupling portion 218 of low-flow fitting 210. As locking collar 244 is threaded onto second coupling portion 218, Luer-type connector 240 including Luer-type fitting 246 is drawn into engagement with fitting 210, and in particular male external sealing surface 250 of Luer-type fitting 246 is drawn into sealing engagement with female internal first sealing surface 216 of low-flow fitting 210.

In the example of FIG. 2C, in which low-flow fitting 210 of insufflation fitting 204 in accordance with this disclosure is fit to low-flow Luer-type connector 240 and associated Luer-type fitting 246, the minimum internal diameter of Luer-type connector 240 limits the flow (rate and/or volume)

of insufflation gas. In particular and as depicted in FIG. 2C, the inner diameter of low-flow Luer-type fitting 246 limits insufflation fluid flow.

Figure 2D:
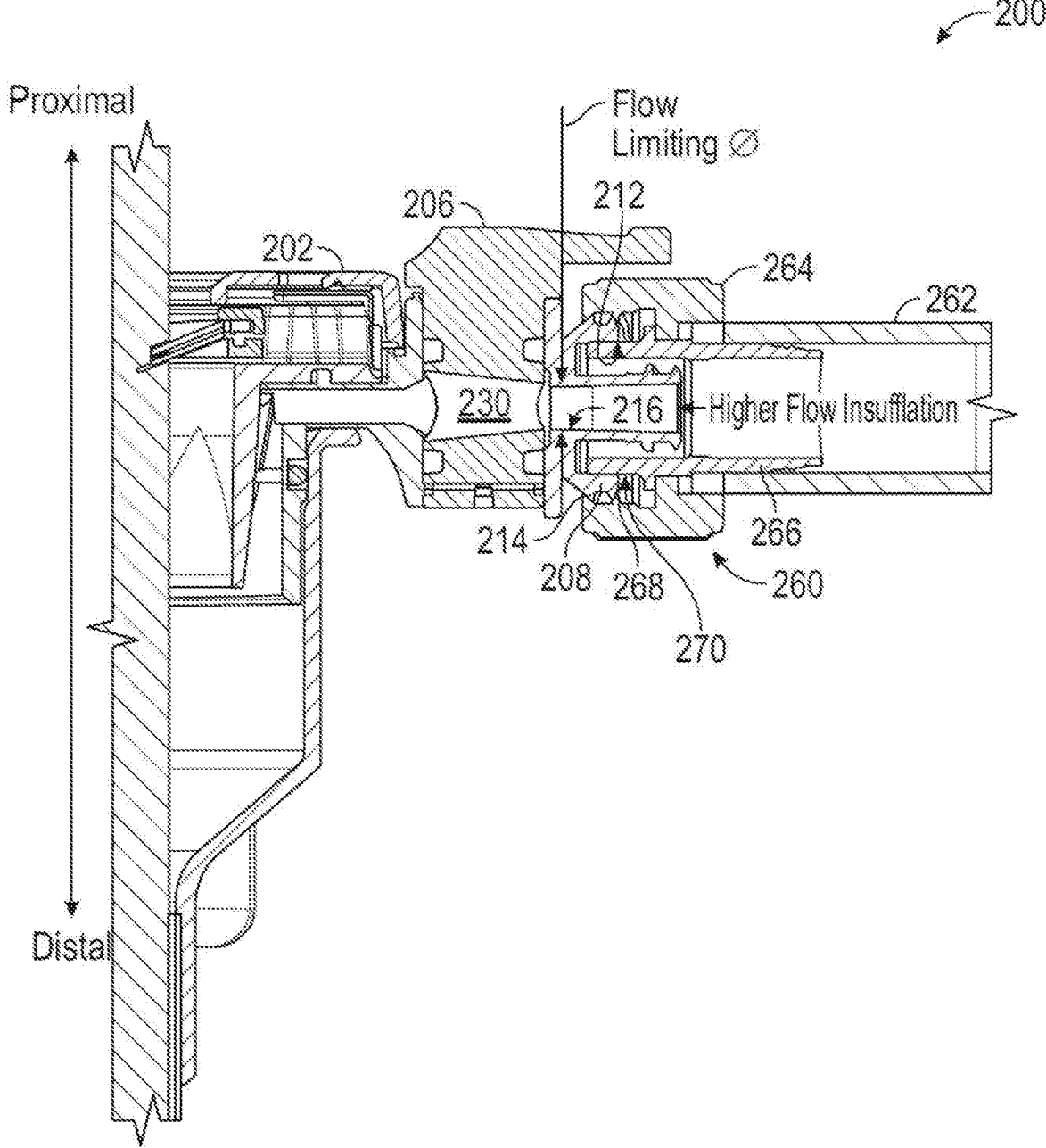
FIG. 2D is a cross-section elevation view depicting the example surgical instrument seal assembly of FIGS. 2A-2C coupled with high-flow connector.

FIG. 2D is a cross-section elevation view depicting example surgical instrument seal assembly 200. In FIG. 2D, seal assembly 200 is coupled with high-flow Luer-type connector 260 connected to high-flow insufflation gas supply line 262. The example of FIG. 2D depicts the manner in which high-flow fitting 208 of insufflation fitting 204 in accordance with this disclosure can be fit to a high-flow Luer-type connector 260 for relatively high-flow (rate and/or volume) insufflation.

High-flow Luer-type connector 260 includes locking collar 264 coupled to high-flow male Luer-type fitting 266, which is coupled to high-flow insufflation line 262. In some examples, high-flow Luer-type connector 260 is packaged with and preconnected to high-flow insufflation line 262. In other examples, however, high-flow Luer-type connector 260 is packaged separately from high-flow insufflation line 262 and is configured to be connected to an insufflation line, e.g., line 262. Locking collar 264 includes coupling portion 268, which can include, for example, threads, lugs, or another locking mechanism. High-flow male Luer-type fitting 266 includes external male sealing surface 270. External sealing surface 270 of male Luer-type fitting 266 is a male tapered surface, the diameter of which decreases as external sealing surface 270 extends toward the free end male Luer-type fitting 266. In FIG. 2D, the diameter of external sealing surface 270 decreases as it extends into high-flow fitting 208.

Locking collar 264 is configured to be coupled to high-flow fitting 208 via first coupling portion 214. For example and as depicted in FIG. 2D, coupling portion 264 of locking collar 264 is threadedably engaged to first coupling portion 214 of high-flow fitting 208. As locking collar 264 is threaded onto first coupling portion 214, high-flow Luer-type connector 260 including high-flow Luer-type fitting 266 is drawn into engagement with fitting 208, and, in particular, male external sealing surface 270 of Luer-type fitting 266 is drawn into sealing engagement with female internal first sealing surface 212 of high-flow fitting 208.

In the example of FIG. 2D in which high-flow fitting 208 of insufflation fitting 204 in accordance with this disclosure is fit to high-flow Luer-type connector 260 and associated high-flow Luer-type fitting 266, the minimum inner diameter of low-flow fitting 210 limits the flow rate and/or volume) of insufflation gas. In particular and as depicted in FIG. 2D, the inner diameter of low-flow fitting 208, which is the minimum inner diameter of second internal sealing surface 216 limits insufflation flow. As noted above, in the example of FIG. 2C, the inner diameter of low-flow Luer-type fitting 246 limits insufflation flow. Because the minimum diameter of second internal sealing surface 216 is larger than the inner diameter of low-flow Luer-type fitting 246, larger insufflation flow is possible with high-flow fitting 208 of insufflation fitting 204 coupled to high-flow Luer-type connector 260 (FIG. 2D) than with low-flow fitting 210 coupled to low-flow Luer-type connector 240.

Figure 3A:
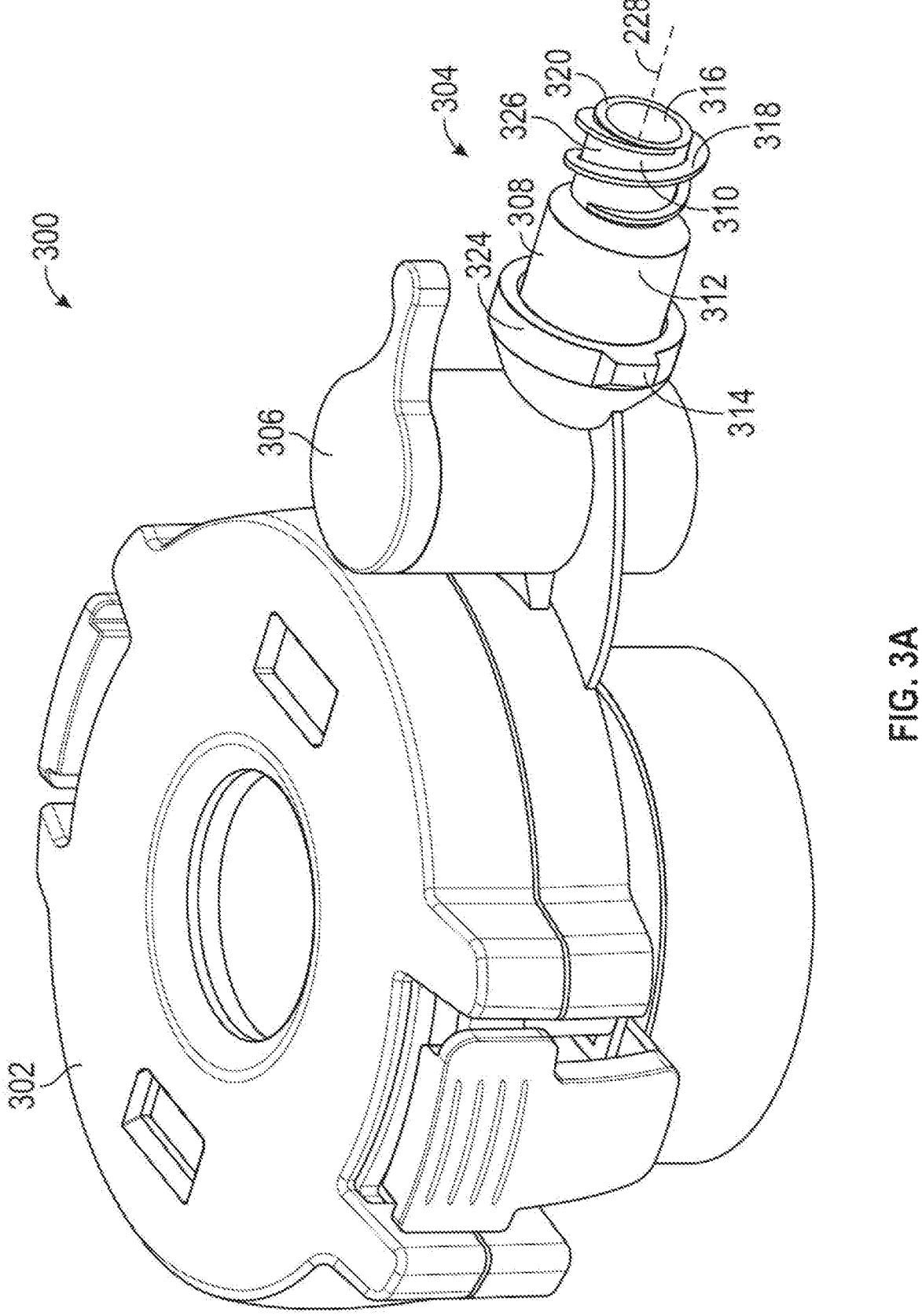
FIG. 3A is a perspective view depicting another example surgical instrument seal assembly.
Figure 3B:
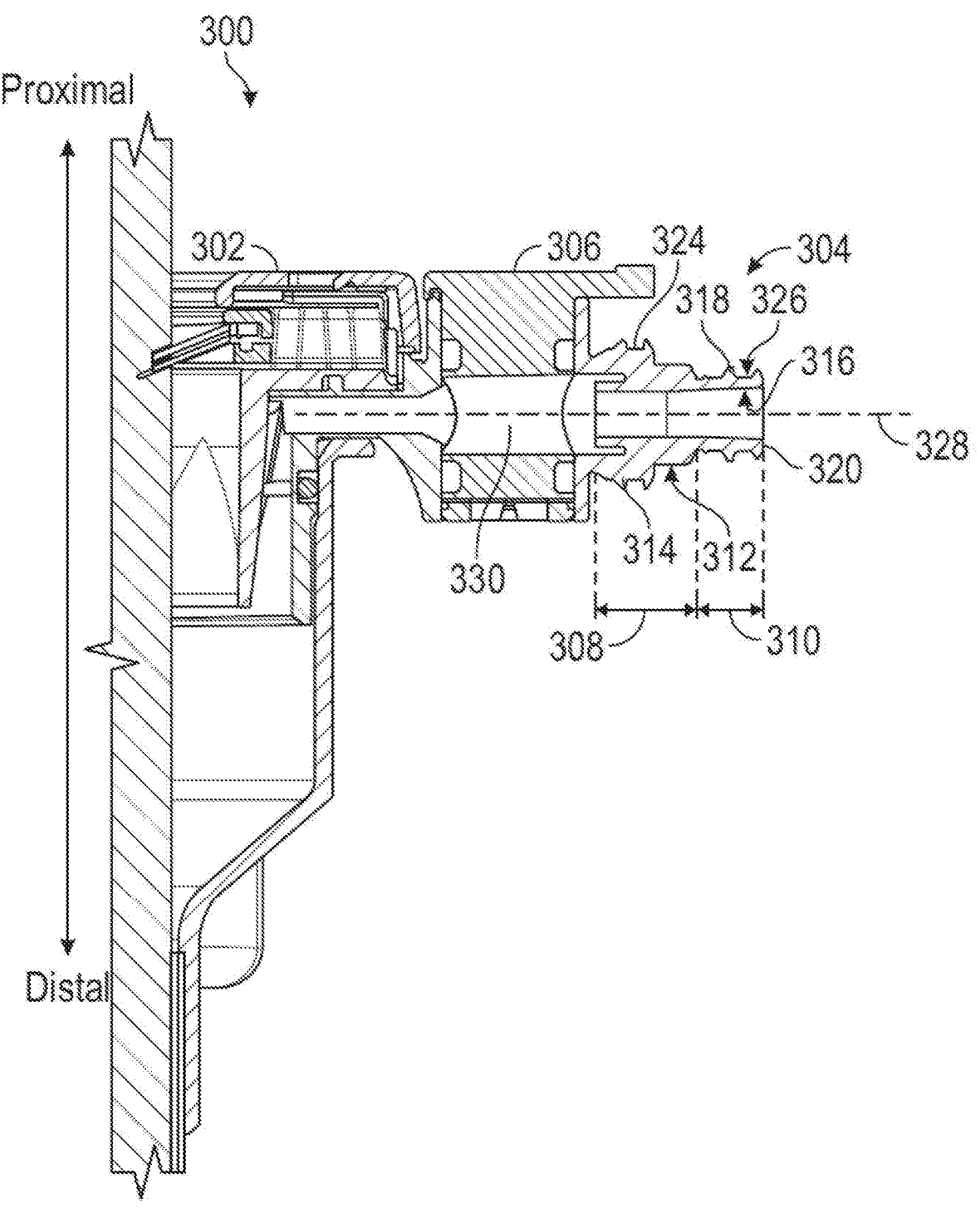
FIG. 3B is a cross-section elevation view depicting the example surgical instrument seal assembly of FIG. 3A.

FIG. 3A is a perspective view depicting example surgical instrument seal assembly 300. FIG. 3B is a cross-section elevation view depicting example surgical instrument seal assembly 300. Referring to FIGS. 3A and 3B, instrument seal assembly 300 includes device body 302, insufflation fitting 304, and valve 306. Valve 306 is fluidically connected to the fluid passageway insufflation fitting 304 and configured to control the flow of insufflation gas into device body 302. Valve 306 can be a variety of different valves including a stopcock valve as depicted in the example of FIGS. 3A and 3B.

Insufflation fitting 304 extends from device body 302, and a flow passage is defined through fitting 404 and into device body 302. Insufflation fitting 304 includes high-flow fitting portion 308 and low-flow fitting portion 310. In the example of insufflation fitting 304, high-flow fitting portion 308 includes external/outer ("male") sealing surface 312 and first coupling portion 314. Low-flow fitting portion 310 includes internal/inner ("female") sealing surface 316 and second coupling portion 318.

Outer sealing surface 312 of high-flow fitting portion 308 is a male tapered surface, the diameter of which decreases from free end 320 of insufflation fitting 304 toward valve 306 and device body 302. Additionally, outer sealing surface 312 is an annular sealing surface. Inner sealing surface 316 of low-flow fitting portion 310 is a female tapered surface, the diameter of which decreases from free end 320 of insufflation fitting 304 toward high-flow fitting portion 308, valve 306, and device body 302. Inner sealing surface 316 is also an annular sealing surface.

First coupling portion 314 is on first external surface 324 of high-flow fitting portion 308, and external surface 324 is located toward valve 306 and device body 302 from external sealing surface 312. First coupling portion 314 and first external surface 324 form a shoulder, which radially offsets coupling portion 314 and surface 324 from external sealing surface 312 and makes the outer diameter of first external surface 324 larger than the outer diameter of external sealing surface 312.

Second coupling portion 318 is on second external surface 326 of low-flow fitting portion 310, and external surface 326 is generally reverse from internal sealing surface 316. First coupling portion 314 of high-flow fitting portion 308 and second coupling portion 318 of low-flow fitting portion 310 include threads. In one example, first coupling portion 314 and second coupling portion 318 include Luer-type threads. In another example, first coupling portion 314 and second coupling portion 318 include another type of thread, lugs, or another locking/coupling mechanism.

High-flow fitting portion 308 extends from and is coupled device body 302. In the example of FIGS. 3A and 3B, high-flow fitting portion 308 is coupled to valve 306, which is coupled to device body 302. Low-flow fitting portion 310 is concentric and integral with, and extends from high-flow fitting portion 310. High-flow fitting portion 308 and low-flow fitting portion 310 share a common axis 328, which also defines a flow path through the flow passage 330 of insufflation fitting 304. High-flow fitting portion 308 is an annulus including outer sealing surface 312, first external surface 324 and an internal surface extending toward body 202 of instrument seal assembly 200 from internal sealing surface 316 of high-flow fitting portion 308. Low-flow fitting portion 310 is an annulus including second external surface 326 and internal sealing surface 316, which extend from high-flow fitting portion 308 to free end 320 of low-flow fitting portion 310.

Although insufflation fitting 304 is depicted in association with an instrument seal assembly/access port device, in other examples insufflation fittings in accordance with this disclosure may be used in association with various other medical devices.

Therefore, in accordance with another inventive aspect a standard medical device fitting, such as female Luer-type fitting, is aligned with a concentric male second fitting. As already described, the female Luer-type fitting receives a corresponding male Luer-type fitting to establish a fluid flow path through the coupled female and male Luer-type fittings, and this flow path is restricted by the Luer-type fitting design. And so the aligned male second fitting can receive a corresponding second female fitting to establish a fluid flow path through the standard female fitting that is not restricted by the standard female/male fitting design.

Figure 3C:
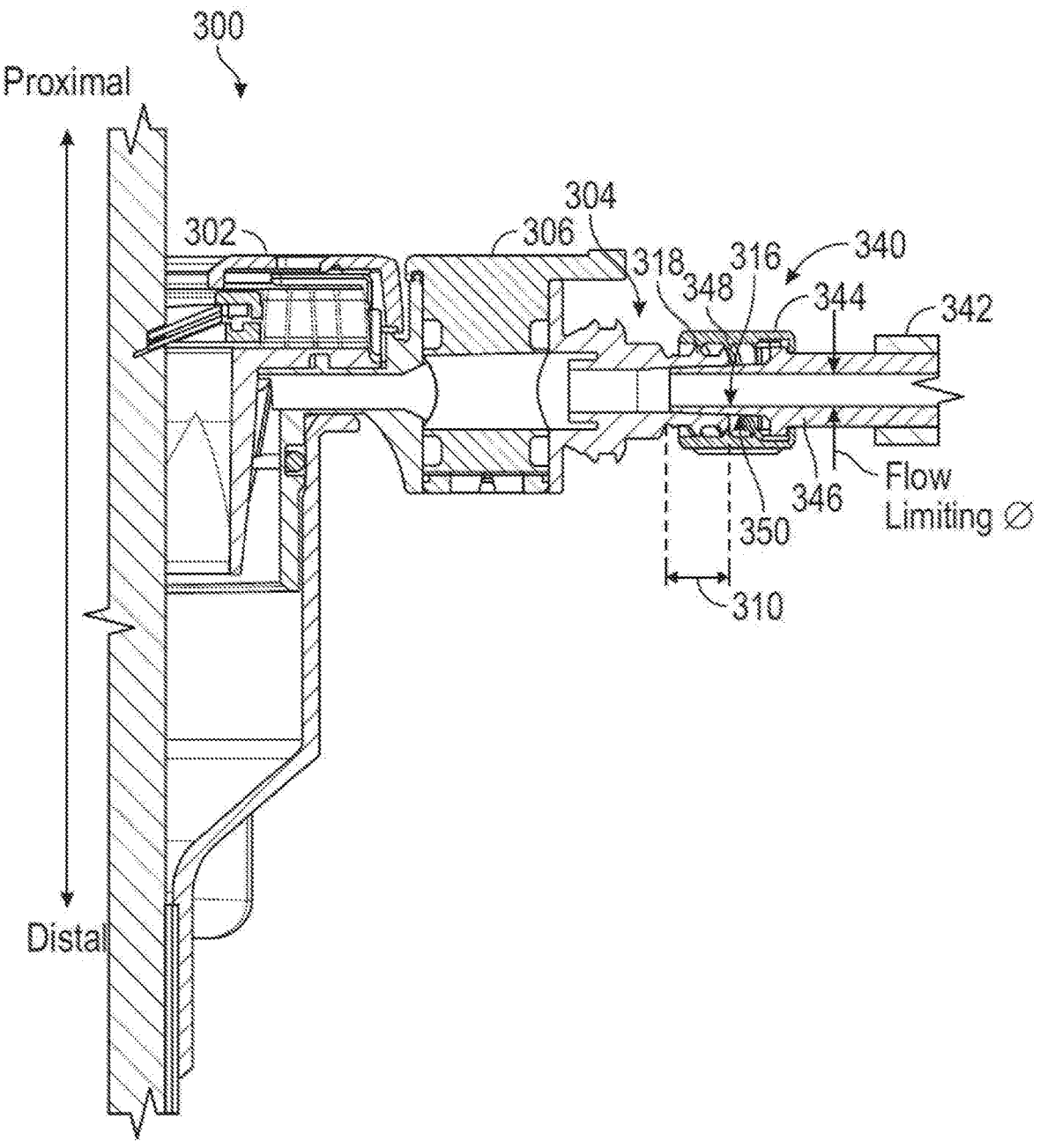
FIG. 3C is a cross-section elevation view depicting the example surgical instrument seal assembly of FIGS. 3A and 3B coupled with a low-flow connector.

FIG. 3C is a cross-section elevation view depicting example surgical instrument seal assembly 300. In FIG. 3C. seal assembly 300 is coupled with a low-flow Luer-type connector 340 connected to low-flow insufflation line 342. The example of FIG. 3C depicts the manner in which insufflation fitting 304 in accordance with this disclosure can be fit to a Luer-type connector 340 for relatively low-flow insufflation (low relative to, e.g., the example of FIG. 2D described below). In particular, the example of FIG. 3C depicts the manner in which low-flow fitting 310 of insufflation fitting 304 can be fit to a Luer-type connector 340 for relatively low-flow insufflation.

Low-flow Luer-type connector 340 includes locking collar 344 coupled to male Luer-type fitting 346, which is coupled to low-flow insufflation line 342. Locking collar 344 includes coupling portion 348, which can include, for example, threads, lugs, or another locking mechanism. Male Luer-type fitting 346 includes external male sealing surface 350. External sealing surface 350 of male Luer-type fitting 346 is a male tapered surface, the diameter of which decreases as external sealing surface 350 extends toward the free end male Luer-type fitting 346. In FIG. 2C, the diameter of external sealing surface 350 decreases as it extends into low-flow fitting portion 210.

Locking collar 344 is configured to be coupled to low-flow fitting portion 310 via second coupling portion 318. For example and as depicted in FIG. 3C, coupling portion 348 of locking collar 344 is threadedably engaged to second coupling portion 318 of low-flow fitting portion 310. As locking collar 344 is threaded onto second coupling portion 318, Luer-type connector 340 including Luer-type fitting 346 is drawn into engagement with fitting portion 310, and, in particular, male external sealing surface 350 of Luer-type fitting 346 is drawn into sealing engagement with female internal sealing surface 316 of low-flow fitting portion 310.

In the example of FIG. 3C in which low-flow fitting portion 310 of insufflation fitting 304 in accordance with this disclosure is fit to low-flow Luer-type connector 340 and associated Luer-type fitting 346, the minimum diameter of Luer-type connector 340 limits the flow (rate and/or volume) of insufflation gas. In particular and as depicted in FIG. 3C, the inner diameter of low-flow Luer-type fitting 346 limits insufflation flow.

Figure 3D:
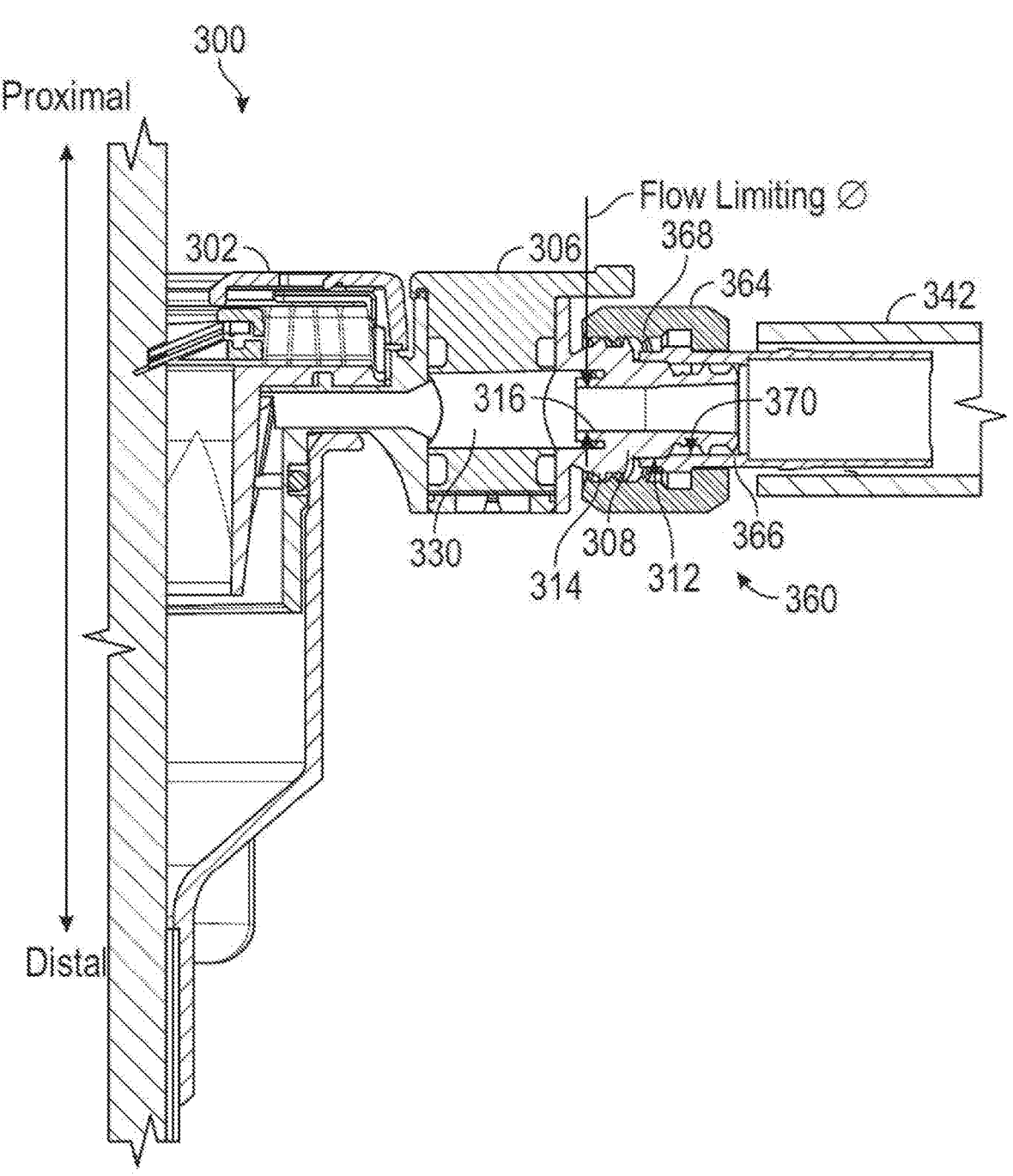
FIG. 3D is a cross-section elevation view depicting the example surgical instrument seal assembly of FIGS. 3A-3C coupled with high-flow connector.

FIG. 3D is a cross-section elevation view depicting example surgical instrument seal assembly 300. In FIG. 3D, seal assembly 300 is coupled with high-flow Luer-type connector 360 connected to high-flow insufflation line 362. The example of FIG. 3D depicts the manner in which high-flow fitting portion 308 of insufflation fitting 304 in accordance with this disclosure can be fit to a high-flow Luer-type connector 360 for relatively high-flow (rate and/or volume) insufflation.

High-flow Luer-type connector 360 includes locking collar 364 coupled to high-flow female Luer-type fitting 366, which is coupled to high-flow insufflation line 362. In some examples, high-flow Luer-type connector 360 is packaged with and preconnected to high-flow insufflation line 362. In other examples, however, high-flow Luer-type connector 360 is packaged separately from high-flow insufflation line 362 and is configured to be connected to an insufflation line, e.g., line 362. Locking collar 364 includes coupling portion 368, which can include, for example, threads, lugs, or another locking mechanism. High-flow female Luer-type fitting 366 includes inner female sealing surface 370. Inner sealing surface 370 of female Luer-type fitting 366 is a female tapered surface, the diameter of which increases as inner sealing surface 370 extends toward the free end of female Luer-type fitting 366, In FIG. 2D, the diameter of inner sealing surface 370 decreases as it extends onto and into sealing engagement with high-flow fitting portion 308.

Locking collar 364 is configured to be coupled to high-flow fitting portion 308 via first coupling portion 314. For example and as depicted in FIG. 2D, coupling portion 364 of locking collar 364 is threadedably engaged to first coupling portion 314 of high-flow fitting portion 308. As locking collar 364 is threaded onto first coupling portion 314, high-flow Luer-type connector 360 including high-flow Luer-type fitting 366 is drawn into engagement with fitting portion 308, and, in particular, female inner sealing surface 370 of Luer-type fitting 366 is drawn into sealing engagement with female inner sealing surface 312 of high-flow fitting portion 308.

In the example of FIG. 3D in which high-flow fitting portion 308 of insufflation fitting 304 in accordance with this disclosure is fit to high-flow Luer-type connector 360 and associated high-flow Luer-type fitting 366, the minimum inner diameter of low-flow fitting portion 310 limits the flow (rate and/or volume) of insufflation gas. In particular and as depicted in FIG. 3D, the inner diameter of low-flow fitting portion 308, which is the minimum diameter of second internal sealing surface 316 limits insufflation flow. As noted above, in the example of FIG. 3C, the inner diameter of low-flow Luer-type fitting 346 limits insufflation flow. Because the minimum inner diameter of second internal sealing surface 316 is larger than the inner diameter of low-flow Luer-type fitting 346, larger insufflation flow is possible with high-flow fitting portion 308 of insufflation fitting 304 coupled to high-flow Luer-type connector 360 (FIG. 2D) than with low-flow fitting portion 310 coupled to low-flow Luer-type connector 340.

Persons of skill in the art will understand that any of the features described above may be combined with any of the other example features, as long as the features are not mutually exclusive. All possible combinations of features are contemplated, depending on clinical or other design requirements. In addition, if manipulating system units are combined into a single system (e.g., telesurgery system), each individual unit may have the same configuration of features, or, one patient-side unit may have one configuration of features and another patient-side unit may have a second, different configuration of features.

The examples (e.g., methods, systems, or devices) described herein may be applicable to surgical procedures, non-surgical medical procedures, diagnostic procedures, cosmetic procedures, and non-medical procedures or applications. The examples may also be applicable for training, or for obtaining information, such as imaging procedures. The examples may be applicable to handling of tissue that has been removed from human or animal anatomies and will not be returned to a human or animal, or for use with human or animal cadavers. The examples may be used for industrial applications, general robotic uses, manipulation of non-tissue work pieces, as part of an artificial intelligence system, or in a transportation system.

The above detailed description includes references to the accompanying drawings, which form a part of the detailed description. The drawings show, by way of illustration, specific embodiments in which the invention may be practiced. These embodiments are also referred to herein as "examples," Such examples may include elements in addition to those shown or described. But, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. Coordinate systems or reference frames are provided for aiding explanation, and implantations may use other reference frames or coordinate systems other than those described herein.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

The claimed invention is:

1. A medical device comprising:

a device body and an insufflation fitting coupled to and extending from the device body;

the insufflation fitting comprising an annular high-flow fitting portion extending away from the device body and an annular low-flow fitting portion integral with and extending from the annular high-flow fitting portion;

the annular high-flow fitting portion comprising a first inner surface and a radially outward male tapered sealing surface generally reverse from the first inner surface;

the annular low-flow fitting portion comprising an inner sealing surface extending from the first inner surface of the annular high-flow fitting portion and a first radially outward surface generally reverse from the inner sealing surface;

the inner sealing surface comprising a female tapered surface including an inner diameter that is largest at an end of the annular low-flow fitting portion distal to the device body and to the annular high-flow fitting portion; and an insufflation gas flow passageway through the insufflation fitting formed by the first inner surface of the annular high-flow fitting portion and the inner sealing surface of the annular low-flow fitting portion extending from the first inner surface of the annular high-flow fitting portion.

2. The medical device of claim 1, wherein the annular low-flow fitting portion is concentric and integral with the annular high-flow fitting portion.

3. The medical device of claim 1, wherein an outer diameter of the radially outward male tapered sealing surface is at least at a location at which the annular high-flow fitting portion.

4. The medical device of claim 1, wherein the radially outward male tapered sealing surface comprises an annular sealing surface.

5. The medical device of claim 1, wherein the inner sealing surface comprises an annular sealing surface.

6. The medical device of claim 1, further comprising:

a high-flow connector surrounding the annular low-flow fitting portion and comprising an inner female sealing surface in sealing engagement with the radially outward male tapered sealing surface of the annular high-flow fitting portion.

7. The medical device of claim 6, wherein the annular high-flow fitting portion further comprises:

a second radially outer surface offset axially from the radially outward male tapered sealing surface toward the device body, and a coupling portion on the second radially outer surface.

8. The medical device of claim 7, wherein the high-flow connector further comprises a locking collar having a coupling portion, the coupling portion of the annular high-flow fitting portion being coupled to the coupling portion of the locking collar of the high-flow connector.

9. The medical device of claim 1, further comprising a low-flow connector comprising a radially outer male sealing surface in sealing engagement with the inner sealing surface.

10. The medical device of claim 9, wherein the annular low-flow fitting portion further comprises a coupling portion on the first radially outward surface.

11. The medical device of claim 10, wherein the low-flow connector further comprises a locking collar having a coupling portion, the coupling portion of the annular low-flow fitting portion being coupled to the coupling portion of the locking collar of the low-flow connector.

12. A medical device fitting comprising:

an annular high-flow fitting portion and an annular low-flow fitting portion integral with and extending away from the annular high-flow fitting portion;

the annular high-flow fitting portion comprising a first inner surface and a radially outward male tapered sealing surface generally reverse from the first inner surface;

the annular low-flow fitting portion comprising an inner sealing surface extending from the first inner surface of the annular high-flow fitting portion and a first radially outward surface generally reverse from the inner sealing surface;

the inner sealing surface comprising a female tapered surface including an inner diameter that is largest at an end of the annular low-flow fitting portion distal to the annular high-flow fitting portion;

a fluid flow passageway through the medical device fitting formed by the first inner surface of the annular high-flow fitting portion and the inner sealing surface of the annular low-flow fitting portion; and a high-flow connector surrounding the annular low-flow fitting portion and comprising an inner female sealing surface in sealing engagement with the radially outward male tapered sealing surface of the annular high-flow fitting portion.

13. The medical device fitting of claim 12, wherein the annular high-flow fitting portion further comprises:

a second radially outer surface offset axially from the radially outward male tapered sealing surface; and a coupling portion on the second radially outer surface.

14. The medical device fitting of claim 13, wherein the high-flow connector further comprises a locking collar having a coupling portion, the coupling portion of the annular high-flow fitting portion being coupled to the coupling portion of the locking collar of the high-flow connector.

15. A medical device fitting comprising:

an annular high-flow fitting portion and an annular low-flow fitting portion integral with and extending away from the annular high-flow fitting portion;

the annular high-flow fitting portion comprising a first inner surface and a radially outward male tapered sealing surface generally reverse from the first inner surface;

the annular low-flow fitting portion comprising an inner sealing surface extending from the first inner surface of the annular high-flow fitting portion and a first radially outward surface generally reverse from the inner sealing surface;

the inner sealing surface comprising a female tapered surface including an inner diameter that is largest at an end of the annular low-flow fitting portion distal to the annular high-flow fitting portion; and a fluid flow passageway through the medical device fitting formed by the first inner surface of the annular high-flow fitting portion and the inner sealing surface of the annular low-flow fitting portion.

16. The medical device fitting of claim 15, further comprising:

a high-flow connector surrounding the annular low-flow fitting portion and comprising an inner female sealing surface in sealing engagement with the radially outward male tapered sealing surface of the annular high-flow fitting portion.

17. The medical device fitting of claim 15, further comprising a low-flow connector comprising a radially outer male sealing surface in sealing engagement with the inner sealing surface.

* * * * *